United States Patent [19]

Homma et al.

[11] 4,252,695

[45] Feb. 24, 1981

[54] HAIR RINSE COMPOSITION

[75] Inventors: Itomi Homma, Funabashi; Masayuki Kanno, Matsudo, both of Japan

[73] Assignee: Kao Soap Co., Ltd., Tokyo, Japan

[21] Appl. No.: 60,271

[22] Filed: Jul. 25, 1979

[30] Foreign Application Priority Data

Jul. 31, 1978 [JP] Japan ................................. 53-93397

[51] Int. Cl.$^3$ .......................... C11D 1/62; A61K 7/06
[52] U.S. Cl. .................................... 252/547; 252/106; 252/546; 252/DIG. 13; 252/DIG. 14; 424/70
[58] Field of Search ............... 252/106, 117, 547, 546, 252/DIG. 13, DIG. 14; 260/567.6 M, 329; 424/70, 32

[56] References Cited

U.S. PATENT DOCUMENTS

| | | | |
|---|---|---|---|
| 3,423,504 | 1/1969 | Birkelo et al. | 424/70 |
| 3,560,507 | 2/1971 | Wakeman et al. | 260/286 |
| 3,579,453 | 5/1971 | Dupre et al. | 252/174.21 X |
| 3,959,461 | 5/1976 | Bailey et al. | 424/70 |
| 3,990,991 | 11/1976 | Gerstein | 252/542 |
| 4,001,394 | 1/1977 | Fogel et al. | 424/70 |
| 4,132,678 | 1/1979 | Iijima et al. | 252/545 |
| 4,134,970 | 1/1979 | Panke et al. | 424/70 |
| 4,160,823 | 7/1979 | Watanabe et al. | 424/70 |
| 4,165,369 | 8/1979 | Watanabe et al. | 424/70 |
| 4,168,302 | 9/1979 | Schoenberg | 424/70 |

OTHER PUBLICATIONS

Kluge, A., Amerian Perfumer & Cosmetics, "Properties of Quaternary Ammonium Satts-their use in Cosmetic & Hair Treatment Preparations", vol. 81, Mar. 1966, pp. 35-40.

*Primary Examiner*—P. E. Willis, Jr.
*Attorney, Agent, or Firm*—Oblon, Fisher, Spivak, McClelland & Maier

[57] ABSTRACT

A hair rinse composition comprising at least one succinic acid derivative and at least one quaternary ammonium salt imparts good feel and combining properties to the hair and reduces hair flying.

4 Claims, No Drawings

HAIR RINSE COMPOSITION

BACKGROUND OF THE INVENTION

1. Field of the Invention

The present invention relates to rinse compositions for use in hair treatment, which are extremely effective. More particularly, this invention relates to a novel hair rinse composition comprising at least one succinic acid derivative as one essential constituent and at least one quaternary ammonium salt as another essential constituent.

2. Description of the Prior Art

Known hair rinse compositions generally include quaternary ammonium salts as effective components and have been used to prevent the hair washed with soaps or shampoos from becoming squeaky, snarled or electrically changed while being combed. Hair rinse compositions are intended primarily to exert flexible, smooth and antistatic properties on the hair. However, it has been proved that the quaternary ammonium salts which are the only effective components of the conventional hair rinse compositions are insufficient to bring the desired flexibility and smoothness to the hair. Currently, because of this problem with the quaternary ammonium salts, they have lost their superiority as constituents for hair rinse compositions.

One more advanced practice lies in incorporating into the compositions of the type described above fats and fatty oils such as higher alcohols, glycerides, liquid paraffins and the like. However, such rinse compositions have still not been quite satisfactory for treating the hair to make the same feel soft and wiry and easy to comb.

With the above defects of the existing prior art techniques in mind, the present inventors have made an intensive study of a variety of succinic acid derivatives, and as a result, have found that some particular succinic acid derivatives can be used in combination with quaternary ammoninum salts, and therefore, form the basis of a novel hair rinse composition which overcomes the defects of the conventional hair rinse compositions and is thus characterized by improved rinsing characteristics such as excellent soft- and wiry-haired touch and combing ability and least hair flying. From this finding, the present invention has been developed.

SUMMARY OF THE INVENTION

This invention provides a hair rinse composition which comprises as a first essential constituent at least one succinic acid derivative represented by the formula (I),

wherein R represents an alkyl or alkenyl group having 6 to 20 carbon atoms, and each of X and Y represents a hydrogen atom, an alkali metal, ammonium or an alkanolamine having 2 or 3 carbon atoms, and as a second essential constituent at least one quaternary ammonium salt represented by the formula (II),

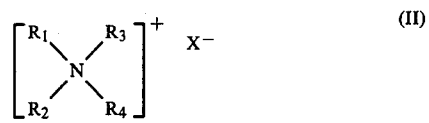

wherein either one or two of $R_1$, $R_2$, $R_3$ and $R_4$ represent long-chain alkyl or long-chain hydroxyalkyl groups having 8 to 20 carbon atoms, the remainder being alkyl of hydroxyalkyl groups having 1 to 3 carbon atoms, benzyl groups, or polyoxyethylene groups having a total addition mole number of less than 10 of ethylene oxide, and X represents a halogen atom or an alkylsulfate group having 1 to 2 carbon atoms.

According to a preferred embodiment of the present invention, the succinic acid derivatives of the formula (I) when combined with the quaternary ammonium salts of the formula (II) greatly enhance the desired rinsing properties. Such properties cannot be attained by the quaternary ammonium salts alone.

The above and other objects, features and advantages of this invention will become apparent from the following description. All percentages in the specification as well as in the appended claims are by weight unless otherwise specified.

DESCRIPTION OF THE PREFERRED EMBODIMENTS

Of the succinic acid derivatives of the formula (I) which are useful as a first group of essential constituents for the composition of this invention, particularly desirable are those in which R represents an alkyl or alkenyl group having 8 to 18 carbon atoms, and each of X and Y represents a hydrogen atom, sodium or triethanolamine. Typical examples of these derivatives include, for instance, dodecylsuccinic acid, salt of oleylsuccinic acid-triethanolamine, sodium salt of iso-stearylsuccinic acid, sodium salt of 2-ethylhexylsuccinic acid, salt of octylsuccinic acid-triethanolamine, myristylsuccinic acid and the like.

It is advantageous to add the first constituents or compounds of the formula (I) in amounts of about 0.1 to 20%, preferably 0.5 to 5% based upon the total weight of the composition.

Typical examples of the quaternary ammonium salts of the formula (II) which are useful as a second group of essential constituents for the composition of this invention include, for instance, distearyldimethylammonium chloride, stearyltrimethylammonium methyl sulfate, N-stearyl-N,N,N-tri(polyoxyethylene)ammonium chloride having a total addition mole number of 3 of ethylene oxide, cetyltriethylammonium bromide, stearyldimethylbenzylammonium chloride and the like.

It is advantageous to add the second constituents or compounds of the formula (II) in amounts of about 0.1 to 20%, preferably 0.5 to 5% based upon the total weight of the composition.

The hair rinse composition according to the invention can be produced by mixing at least one succinic acid derivative of the formula (I) with at least one quaternary ammonium salt of the formula (II), and dissolving or dispersing the resulting mixture in a liquid carrier such as water or other suitable solvent such as ethylene glycol, ethyl alcohol, glycerine, propylene glycol or the like. In such instance, the composition prepared in the form of an aqueous solution of 5% in concentration should be adjusted to have a pH of 3 to 8, as is commonly known in the art.

For the hair rinse composition of this invention, other suitable adjuvants can be employed which include, for instance, fats and fatty oils such as higher alcohols, glycerides, hydrocarbons and esters, nonionic surface-active agents, germicides, pigments, perfumes and the like, all of which have been widely used in the conventional hair rinse compositions. These adjuvants may be included individually or in combination in any convenient manner. Accordingly, it will be noted that the composition of this invention can be in the form of a solution, suspension, dispersion or emulsion in aqueous media.

Having generally described the invention, a further understanding can be obtained by reference to certain specific Examples which are provided herein for purposes of illustration only and are not intended to be construed as limiting.

EXAMPLE I

Two hair rinse solutions were prepared by dissolving 10 g of each of the test compositions described below in 500 ml of water. Two tresses or bundles of hairs bound together and washed with a commercially available shampoo, each tress being 20 cm in length and 20 g in weight, were immersed in each of the test solutions for 30 seconds. Thereafter, the tresses were washed with running water for 30 seconds and wiped with a towel. For purposes of comparison, one of the wet tresses was used as it was for estimation, whereas the other was dried by being allowed to stand for 12 hours at room temperature.

The results obtained are shown in Table 1.

The test hair rinse compositions were formulated as follows:

|  | A | B |
|---|---|---|
| Distearyldimethylammonium chloride | 2.0% | 2.0% |
| Monostearyltrimethylammonium chloride | 0.5% | 0.3% |
| Myristyl alcohol | 0.3% | 0.3% |
| Dodecylsuccinic acid | — | 1.0% |
| Water | balance | balance |
| pH (5% solution) | 5.0 | 5.0 |

A: Control
B: Present composition

An estimation of the finished rinsing properties by the test compositions was conducted as follows:

(1) Soft- and wiry-haired touch

This property was estimated by a panel of ten female panelists who actually touched each of the treated tresses with their own fingers and finally felt to be satisfactory.

(2) Combing ability

This property was estimated from the stresses applied to each tress hung on a strain gauge when combed at a speed of one second per stroke.

(3) Hair flying

After being used in connection with combing ability, the tresses were further allowed to stand for 24 hours in a chamber having an ambient temperature of 25° C. and a relative humidity of 25%. Each of the tresses was then brushed with a nylon hair brush, and at this time hair flying was observed. Conveniently, the symbol o denotes non-occurrence, whereas x denotes occurrence in Table 1.

TABLE 1

| Estimation | Wet | | Dry | |
|---|---|---|---|---|
| | A | B | A | B |
| Soft-and wiry-haired touch (person) | 0 | 10 | 3 | 7 |
| Combing ability (g) | 90.5 | 60.3 | 114.4 | 81.3 |
| Hair flying | — | — | X | O |

EXAMPLE II

Two hair rinse solutions were prepared having the test compositions described below. Finished rinsing properties were estimated by the same test methods used in Example I.

The results obtained are shown in Table 2.

The test compositions were formulated as follows:

|  | C | D |
|---|---|---|
| Stearyldimethylbenzylammonium chloride | 1.0% | 1.0% |
| Salt of oleylsuccinic acid-triethanolamine | — | 1.0% |
| Cotton seed oil | 0.5% | 0.5% |
| Cationic polymerized cellulose (Polymer-JR-400) | 1.0% | 1.0% |
| Water | balance | balance |
| pH (5% solution) | 5.0% | 5.0% |

C: Control
D: Present composition

TABLE 2

| Estimation | Wet | | Dry | |
|---|---|---|---|---|
| | C | D | C | D |
| Soft- and wiry-haired touch (person) | 1 | 9 | 2 | 8 |
| Combing ability (g) | 73.5 | 42.1 | 86.0 | 52.1 |
| Hair flying | — | — | X | O |

What is claimed is:

1. A hair rinse composition comprising as a first essential constituent 0.1 to 20% by weight of at least one succinic acid derivative represented by the formula (I),

$$R-CHCOOX \atop | \atop CH_2COOY \qquad (I)$$

wherein R represents an alkyl or alkenyl group having 6 to 20 carbon atoms, and each of X and Y represents a hydrogen atom, an alkali metal, ammonium or an alkanolamine having 2 or 3 carbon atoms, and as a second essential constituent 0.1 to 20% by weight of at least one quaternary ammonium salt represented by the formula (II)

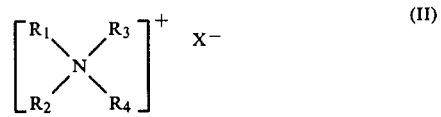

$$\left[ \begin{array}{cc} R_1 & R_3 \\ \diagdown & \diagup \\ & N \\ \diagup & \diagdown \\ R_2 & R_4 \end{array} \right]^+ X^- \qquad (II)$$

wherein either one or two of $R_1$, $R_2$, $R_3$ and $R_4$ represent long-chain alkyl or long-chain hydroxyalkyl groups having 8 to 20 caron atoms, the remainder being alkyl or hydroxyalkyl groups having 1 to 3 carbon atoms, benzyl groups or polyoxyethylene groups having a total addition mole number of less than 10 of ethylene oxide, and X represents a halogen atom or an alkylsulfate group having 1 to 20 carbon atoms.

2. The hair rinse composition according to claim 1, wherein said first essential constitutent is included in amounts of 0.5 to 5% based upon the total weight of the composition.

3. The hair rinse composition according to claim 1, wherein said second essential constituent is included in amounts of 0.5 to 5% based upon the total weight of the composition.

4. The hair rinse composition according to claim 1, wherein said first essential constituent is a succinic acid derivative in which R represents an alkyl or alkenyl group having 8 to 18 carbon atoms, and each of X and Y represents a hydrogen atom, sodium or triethanolamine.

* * * * *